(12) United States Patent
Kobayashi et al.

(10) Patent No.: US 6,326,405 B1
(45) Date of Patent: Dec. 4, 2001

(54) ANTICANCER AGENT

(75) Inventors: Eiji Kobayashi; Nobuto Koyama; Ikunoshin Kato, all of Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/443,089

(22) Filed: Nov. 18, 1999

Related U.S. Application Data

(63) Continuation of application No. PCT/JP98/03223, filed on Jul. 16, 1998.

(30) Foreign Application Priority Data

Jul. 25, 1997 (JP) .................................................. 9-213839

(51) Int. Cl.[7] ........................... A61K 31/12; C07C 49/395
(52) U.S. Cl. ......................... 514/690; 514/729; 568/303; 568/379
(58) Field of Search ................... 568/303, 379; 514/690, 729

(56) References Cited

FOREIGN PATENT DOCUMENTS 6321831    11/1994   (JP) .

OTHER PUBLICATIONS

Aldrich catalog, p. 427, 1996.*
International Search Report for International Application PCT/JP98/03223, Oct. 6, 1998.

Seiichi Inayama et al., "Structure and Antitumor Activity Relationship of 2–Arylidene–4–cyclopentene–1,3–diones and 2–Arylideneindan–1,3–diones," *Journal of Medicinal Chemistry*, 1976, vol. 19, No. 3, pp. 433–436.
International Preliminary Examination Report, International Application No. PCT/JP98/03223, Jul. 27, 1999.

* cited by examiner

*Primary Examiner*—Sreeni Padmanabhan
(74) *Attorney, Agent, or Firm*—Kolisch Hartwell Dickinson McCormack & Heuser

(57) ABSTRACT

An anticancer agent in which 4-cyclopentene-1,3-dione represented by the following formula [I] and/or 4-hydroxy-2-cyclopentenone represented by the following formula [II] are/is effective component(s).

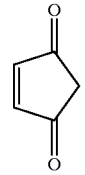

[I]

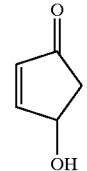

[II]

4 Claims, No Drawings

ANTICANCER AGENT

This application is a Continuation application of PCT/JP98/03223 filed Jul. 16, 1998.

TECHNICAL FIELD

The present invention relates to the pharmaceutical agents which use specific compound having an anticancer action and an apoptosis-inducing action as an effective component.

PRIOR ART

Pharmaceutical agents which have been used in clinical therapy include many agents such as anticancer agents, antibiotic substances, immunopotentiators, immunomodulators, etc. (such as alkylating agents, antimetabolites and plant alkaloids) but it can be hardly said that such a drug therapy has been completely established already.

Among those agents, prostaglandin A and J having a cyclopentenone ring among the prostaglandins derived from natural substances have been reported to have a possibility of being used as highly safe anticancer agents due to their inhibition of DNA synthesis and various derivatives of them have been synthesized (refer to the Japanese Laid-Open Patent Publication Sho-62/96438).

In recent years, a mode of apoptosis has been drawing the attention concerning the death of cell tissues.

Unlike necrosis which is a pathogenic death of cells, apoptosis is believed to be a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein. If such apoptosis can be expressed in desired tissues or cells, it will be now possible to exclude the unnecessary or pathogenic cells from living body in their natural form and that will be significantly meaningful.

PROBLEMS TO BE SOLVED BY THE INVENTION

An object of the present invention is to offer an anticancer agent and an apoptosis-inducing agent in which a compound having an α, β-unsaturated carbonyl group in its five-membered ring is an effective component.

MEANS TO SOLVE THE PROBLEMS

The present inventors have carried out an intensive investigation for achieving the above object and, as a result, they have found the compounds having an anticancer action, an apoptosis-inducing action, etc. whereupon they have accomplished the present invention.

The first feature of the present invention relates to an anticancer agent in which 4-cyclopentene-1,3-dione represented by the following formula [I] and/or 4-hydroxy-2-cyclopentenone represented by the following formula [III] are/is effective components(s).

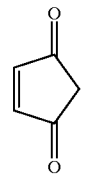

[I]

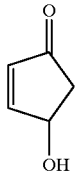

[II]

The second feature of the present invention relates to an apoptosis-inducing agent in which 4-cyclopentene-1,3-dione represented by the above formula [I] and/or 4-hydroxy-2-cyclopentenone represented by the above formula [II] are/is effective component(s).

BEST MODE FOR CARRYING OUT THE INVENTION

The present invention will now be specifically illustrated as hereunder.

Each of 4-cyclopentene-1,3-dione represented by the formula [I] and 4-hydroxy-2-cyclopentenone represented by the formula [II] is a known compound and can be manufactured by known methods or, alternatively, commercially available compounds may be used.

With regard to 4-cyclopentene-1,3-dione, it can be synthesized by a method by G. H. de Puy, et al. [*J. Am. Chem. Soc.*, 82, 631 and 2909 (1960)], a method by V. A. Mirinov, et al. [*Chemical Abstracts*, 18178e (1973)] or a method by Kirschke, et al. [*J. Prakt. Chem.*, 317, 807 (1975)] or a commercially available substance such as a product by Aldrich (16, 168-3) may be used.

With regard to 4-hydroxy-2-cyclopentenone, it can be prepared by reduction of 4-cyclopentene-1,3-dione with cerium (III) chloride or with sodium borohydride. Known synthetic methods therefor are a method by T. Tanaka, et al. [*Tetrahedron*, 32, 1713 (1976)], a method by M. Nara, et al. [*Tetrahedron*, 36, 3161 (1980)] and a method by M. Gill, et al. [*Aust. J. Chem.*, 34, 2587 (1981)]. Any of (R)-substance, (S)-substance and a mixture thereof may be used as the 4-hydroxy-2-cyclopentenone.

4-Cyclopentene-1, 3-dione and 4-hydroxy-2-cyclopentenone have an anticancer action and a cell growth inhibiting action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. These compounds can be used in anticancer agent as an effective component and also have an apoptosis-inducing action to these cancer cells. Mechanism of the cell growth inhibiting action to cancer cells of these compounds used in the present invention does not limit the scope of the present invention at all and, for example, an apoptosis inducing action to cancer cells is covered by the present invention as well.

The anticancer agent of the present invention uses 4-cyclopentene-1,3-dione and/or 4-hydroxy-2- cyclopentenone having an anticancer action as an effective component and when these components are made into a pharmaceutical preparation by compounding with known pharmaceutical carriers, it is now possible to prepare an anticancer agent.

Generally, at least one of these is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where 4-cyclopentene-1,3-dione and/or 4-hydroxy-2-cyclopentenone which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of 4-cyclopentene-1,3-dione and/or 4-hydroxy-2-cyclopentenone contained in the preparation is from 0.1 $\mu$g to 5 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

4-Cyclopentene-1,3-dione and/or 4-hydroxy-2-cyclopentenone of the present invention has an apoptosis inducing action and an apoptosis inducer containing 4-cyclopentene-1,3-dione and/or 4-hydroxy-2-cyclopentenone as an effective component can be prepared. The apoptosis inducer can be made into pharmaceutical preparations according to the above-mentioned anticancer agent and is administered by the same manner as in the case of the anticancer agent.

Dose as the apoptosis inducer is appropriately decided by its form of preparation, method of administration, purpose of the use and age, body weight and symptom of the patient to be treated and it is not constant but, usually, the amount of 4-cyclopentene-1,3-dione and/or 4-hydroxy-2-cyclopentenone contained in the preparation is from 0.1 $\mu$g to 2 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The apoptosis inducer of the present invention is quite useful since it is capable of induction of apoptosis in desired tissues and cells and able to exclude the unnecessary cells or the pathogenic cells from living organisms in a natural state.

Thus, the apoptosis inducer of the present invention is effective in elimination of, for example, virus-infected cells, cancer cells and autoreactive lymphocytes in the patients suffering from autoimmune diseases and, as a result of expression of apoptosis in desired tissues or cells, it is now possible to eliminate the unnecessary or harmful cells from living body in their natural form. Examples of the diseases for which the apoptosis inducer of the present invention is effective are systemic lupus erythematosus, immune-intervening glomerular nephritis, multiple sclerosis, collagen disease and other autoimmune diseases as well as rheumatism.

The apoptosis inducer of the present invention can be used in a method for the induction of apoptosis. Thus, when 4-cyclopentene-1,3-dione and/or 4-hydroxy-2-cyclopentenone are/is used as an effective component, it is possible to induce apoptosis and said method is useful, for example, for elucidation of a mechanism for apoptosis induction and for screening of apoptosis inducers and apoptosis induction inhibitors.

Moreover, 4-cyclopentene-1,3-dione and 4-hydroxy-2-cyclopentenone have a topoisomerase inhibiting action. Both of those compounds have an $\alpha$, $\beta$-unsaturated carbonyl group. The present inventors have further investigated the topoisomerase inhibiting action of the compounds having an $\alpha$, $\beta$-unsaturated carbonyl group as such and have found that a compound having an $\alpha$, $\beta$-unsaturated carbonyl group has a strong inhibiting action to topoisomerase. Thus, a topoisomerase inhibitor containing a compound having an $\alpha$, $\beta$-unsaturated carbonyl group as an effective component is offered by the present invention. There is no particular limitation for the compound having an $\alpha$, $\beta$-unsaturated carbonyl group used for the said topoisomerase inhibitor but maleimide, 4,5-dihydroxy-2-cyclopentene-1-one and 4-tert-butylcyclopentenone ether represented by the following formula [III] and the like may be exemplified in addition to 4-cyclopentene-1,3-dione and 4-hydroxy-2-cyclopentenone.

[III]

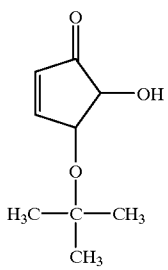

The above-mentioned topoisomerase inhibitor is made into a pharmaceutical preparation using a compound having an α, β-unsaturated carbonyl group as an effective component by a similar manner as mentioned already under the paragraphs concerning an anticancer agent and can be administered by a method similar to that of an anticancer agent. The above topoisomerase inhibitor specifically inhibits topoisomerase II which is transiently expressed only during the stage of division of normal cells while it becomes highly expressible throughout the whole cell period as a result of canceration of the cell and is useful as a highly selective inhibitor to topoisomerase II. It is also useful as an anticancer agent via a specific inhibiting action to topoisomerase II. In addition, a method for inhibition of topoisomerase using the said topoisomerase inhibitor is useful in biochemical studies and in screening of anticancer agents, etc.

4-Cyclopentene-1,3-dione and 4-hydroxy-2-cyclopentenone used in the present invention are the compounds having various physiological actions such as an anticancer action, a suppressing action to the growth of cancer cells, a suppressing action to the growth of abnormal cells, an apoptosis-inducing action, a topoisomerase inhibiting action and a suppressing action to synovial cells and, as a pharmaceutical preparations containing such compounds as effective components, a suppressor for the growth of cancer cells, a suppressor for the growth of abnormal cells, a suppressor for synovial cells, etc. may be offered in addition to an anticancer agent, an apoptosis-inducing agent and a topoisomerase inhibitor.

4-Cyclopentene-1,3-dione and 4-hydroxy-2-cyclopentenone used in the present invention have a suppressing action to the growth of cancer cells, an apoptosis-inducing action, etc. and food or beverage where at least one compound selected from those compounds is contained therein, diluted therewith or added thereto is useful as food or beverage having anticancer and apoptosis-inducing actions.

There is no particular limitation for the method of manufacturing the food or beverage of the present invention but manufacture by means of cooking, processing and commonly used manufacturing method of food or beverage may be exemplified so far as the food or beverage manufactured thereby contains 4-cyclopentene-1,3-dione and 4-hydroxy-2-cyclopentenone having anticancer and apoptosis-inducing actions.

In the case of 4-cyclopentene-1,3-dione used in the present invention, no dead case is noted even upon a single administration per os to mice at a dose of 10 mg/kg. In the case of 4-hydroxy-2-cyclopentenone, no dead case is noted even upon a single administration per os to mice at a dose of 100 mg/kg. Moreover, in the cases of 4,5-dihydroxy-2-cyclopentene-1-one and 4-tert-butylcyclopentenone ether, no dead case is noted even upon a single administration per os to mice at a dose of 10 mg/kg each.

EXAMPLES

The present invention will now be more specifically illustrated by way of the following examples although the present invention is not limited to those examples at all.

Example 1

(1) Each 10 μl of a 250 mM, 125 mM, 62.5 mM, 31.3 mM, 15.6 mM, 7.81 mM, 3.91 mM, 1.95 mM, 977 μM, 488 μM, 244 μM, 122 μM, 61.0 μM, 30.5 μM or 15.3 μM solution (in a 70% aqueous solution of ethanol) of 4-cyclopentene-1,3-dione or 4-hydroxy-2-cyclopentenone or a 70% aqueous solution of ethanol as a control was added to each well of a 96-well microtiter plate and dried with air. Promyelocytic leukemia cell strain HL-60 (ATCC CCL-240) was suspended in a concentration of $1 \times 10^5$ cells/ml in an RPMI 1640 medium (manufactured by BioWhittaker) containing 10% of fetal bovine serum (manufactured by JRH) treated at 56° C. for 30 minutes, each 100 μl thereof were placed in each well of the above microtiter plate and incubated at 37° C. for 48 hours in the presence of 5% of $CO_2$. An aqueous solution of sodium chloride (10 μl) with a phosphate buffer containing 5 mg/ml of 3-(4,5-dimethylthiazol-2-yl)-2,5-diphenyltetrazolium bromide (MTT; manufactured by Sigma) was added thereto, an incubation was carried out for four hours more and the state of growth of the cells was observed under a microscope. In the meanwhile, 100 μl of 2-propanol containing 0.04N HCl were added thereto followed by well stirring and an absorbance at 590 nm was measured.

The result was that the growth of the HL-60 cells were completely suppressed and the formation of apoptic body was noted in the sections where 30.5 μM of 4-cyclopentene-1,3-dione were added (final concentration: 3.05 μM) and where 122 μM of 4-hydroxy-2-cyclopentenone were added (final concentration: 12.2 μM) . In the sections to which higher concentrations than those were added, no cell growth was noted while, in the sections to which lower concentrations were added, the same cell growth as in the section to which a 70% aqueous solution of ethanol (a control) was added was noted.

(2) HL-60 (ATCC CCL-240) incubated at 37° C. in an RPMI 1640 medium containing 10% of fetal bovine serum was suspended in an RPMI 1640 medium ina concentration of $2.5 \times 10^5$ cells/ml.

To 5 ml of this suspension were added each 10 μl of a 70% ethanolic solution of 0.05 mM, 0.5 mM, 5 mM and 50 mM 4-cyclopentene-1,3-dione and 0.05 mM, 0.5 mM, 5 mM and 50 mM of 4-hydroxy-2-cyclopentenone and then incubation was carried out at 37° C. for 24 hours in the presence of 5% of carbon dioxide.

The incubated cells were observed under an optical microscope and aggregation of nuclei, shrinkage of cells and formation of apoptic body were confirmed in the incubated cells to which 1 μM (final concentration) of 4-cyclopentene-1,3-dione or 10 μM (final concentration) of 4-hydroxy-2-cyclopentenone was added. Incidentally, in the incubated cells to which 10 μl of a 70% ethanolic solution (a control) were added, such phenomena were not noted.

After that, the cells incubated for 24 hours and 48 hours by the same method as above were used and measurement of apoptosis cells using FACScan by a method mentioned in pages 129–130 of "Protocol for Experiments on Apoptosis"

(in "Experimental Protocol Series" which is a special issue of Saibo Kogaku, published by Shujunsha) and analysis of fragmentation of DNA by a method mentioned in pages 61–63 of "Biomanual UP Series—New Experimental Method of Apoptosis" (published by Yodosha) were carried out. The result was that apoptosis cells were noted in the incubated cells to which 1 μM (final concentration) or more 4-cyclopentene-1,3-dione or 10 μM (final concentration) or more 4-hydroxy-2-cyclopentenone was added while fragmentation of DNA was noted in the incubated cells to which 1 μM 4-cyclopentene-1,3-dione or 10 μM 4-hydroxy-2-cyclopentenone was added. Incidentally, in the incubated cells to which 10 μl of a 70% ethanolic solution (a control) were added, such phenomena were not noted.

(3) A part of the cells incubated for 24 hours by the same method as in Example 1–(2) was sampled, dyed with a 0.4% Trypan Blue and observed under an optical microscope, numbers of living cells which were not dyed and those of dead cells which were dyed in blue were counted and the concentrations of 4-cyclopentene-1,3-dione and 4-hydrodxy-2-cyclopentenone where the survival rate was 50% were calculated. The said concentrations (survival rate$_{50\%}$ μM) are shown in Table 1.

TABLE 1

| Name of the Substance | Survival Rate$_{50}$ (μM) |
|---|---|
| 4-Cyclopentene-1,3-dione | 2.55 |
| 4-Hydrodxy-2-cyclopentenone | 25.5 |

It is apparent from the above that 4-cyclopentene-1,3-dione and 4-hydrodxy-2-cyclopentenone show a suppressing action to the growth of cancer cells and an apoptosis inducing action at the above-mentioned concentrations.

Example 2

(1) D-Glucuronic acid (10 g; G 5269 manufactured by Sigma) was dissolved in one liter of water, heated at 121° C. for four hours and concentrated in vacuo to about 10 ml. To this were added 40 ml of the upper layer of a 3:2:2 mixture of butyl acetate, acetic acid and water followed by mixing and subjecting to a centrifugal separation and the resulting supernatant liquid obtained thereby was concentrated in vacuo to about 10 ml.

The above extract was applied to a silica gel BW-300 SP (2×28 cm; manufactured by Fuji Silisia Kagaku) for a column chromatography and a separation was carried out at a flow rate of 5 ml/minute using an upper layer of a 3:2:2 mixture of butyl acetate, acetic acid and water as an eluent at a pressure of 0.2 kg/cm$^2$ using a compressor. Fractionation was carried out for making one fraction 10 ml and a part of each fraction was analyzed by means of a thin layer chromatography whereupon 4,5-dihydroxy-2-cyclopentene-1-one of a high purity was contained in the 61st to the 80th fractions. Those fractions were collected, concentrated in vacuo and extracted with 40 ml of chloroform and the extract was concentrated to give 100 mg of 4,5-dihydroxy-2-cyclopentene-1-one.

(2) 4,5-Dihydroxy-2-cyclopentene-1-one (44 mg) and 287 mg of tert-butyl 2,2,2-trichloroacetimidate (36,478–9; manufactured by Aldrich) were dissolved in 2.5 ml of dichloromethane in an argon stream. To this was gradually added 1 ml of a solution of 28 μl/ml of boron trifluoride diethyl ether complex in dichloromethane with stirring. After stirring at room temperature for eight hours, the mixture was concentrated in vacuo and 4-tert-butylcyclopentenone ether was purified by means of a silica gel thin layer chromatography using chloroform and methanol (19:1) as a developer. Incidentally, the Rf value and the yield of 4-tert-butylcyclopentenone ether were 0.35 and 9.2%, respectively.

(3) 4-Cyclopentene-1,3-dione, 4-hydroxy-2-cyclopentenone, maleimide (12,958-5 manufactured by Aldrich), 4,5-dihydroxy-2-cyclopentene-l-one and 4-tert-butylcylopentenone ether were used as the compounds having an α, β-unsaturated carbonyl group and their topoisomerase inhibiting activity was measured as follows.

(i) A mixture of 2 μl of topoisomerase II (2 units/μl; manufactured by TopoGEN), 2 μl of a buffer in a ten-fold concentration [0.5M Tris-HCl (pH 8.0), 1.2M KCl, 0.1M MgCl$_2$, 5 mM adenosine triphosphate and 5 mM dithiothreitol], 2 μl of bovine serum albumin (manufactured by Takara Shuzo), 11 μl of distilled water and 2 μl of distilled water (a control) or 4-cyclopentene-1,3-dione, 4-hydroxy-2-cyclopentenone, maleimide, 4,5-dihydroxy-2-cyclopentene-1-one or 4-tert-butylcyclopentenone ether prepared in various concentrations with water was made to react with 1 μl of 0.25 μg/μl of pBR322 DNA (manufactured by Takara Shuzo) at 37° C. After the reaction for 30 minutes, the reaction was stopped by adding 2 μl aqueous solution of 1% sodium dodecylsulfate, 50% glycerol and 0.02% Bromophenol Blue.

The above reaction solution (20 μl) was applied to a 1% agarose gel prepared from agarose L03 (manufactured by Takara Shuzo) and a TAE buffer [40 mM Tris, 5 mM sodium acetate and 1 mM disodium ethylenediaminetetraacetate (EDTA); adjusted to pH 7.8 by acetic acid] and an electrophoresis was carried out in a TAE buffer. After the electrophoresis, the gel was dipped in a 1 μg/ml aqueous solution of ethidium bromide and irradiated with an ultraviolet ray to observe the electrophoretic pattern of DNA. Incidentally, in a control where water was added, DNA was completely changed from a supercoiled type to a relaxed type but, when topoisomerase II activity is inhibited, the change from the supercoiled type to the relaxed type is partially or completely inhibited.

The result was that, in a control where water was added, DNA was changed from the supercoiled type to the relaxed type completely while, in the cases of 50 μM or more 4-cyclopentene-1,3-dione, 100 μM or more 4-hydroxy-2-cyclopentenone, 1 μM or more maleimide, 50 μM or more 4,5-dihydroxy-2-cyclopentene-1-one and 500 μM or more 4-tert-butylcyopentenone ether, the change of DNA from the supercoiled type to the relaxed type was partially or completely inhibited whereby the topoisomerase II inhibiting activity of the compounds having an α, β-unsaturated carbonyl group was confirmed.

(ii) A topoisomerase I inhibiting activity of each of the compounds was measured by the same method as in Example 2-(3)-(i) except that, instead of topoisomerase II, topoisomerase I [manufactured by TopoGEN; 0.01 unit/μl] was used and, as a buffer of a ten-fold concentration, 100 mM Tris-HCl (pH 7.9), 10 mM EDTA, 1 mM spermidine and 50% glycerol were used.

The result was that, in the control where water was added, DNA was completely changed from the supercooled type to the relaxed type while, in the cases of 1000 μM or more 4-cyclopentene-1,3-dione, 1000 μM or more 4,5-dihydroxy-2-cycopentene-l-one and 1000 μM or more maleimide, the change of DNA from the supercoiled type to the relaxed type was partially inhibited whereby their topoisomerase I inhibiting activity was confirmed.

As such, the compounds having an α, β-unsaturated carbonyl group showed a specific inhibiting activity to topoisomerase II which is transiently expressed only in a stage of division in normal cells and becomes highly expressible throughout the whole cell cycle as a result of canceration.

Example 3

Mouse solid cancer Meth A ($2 \times 10^6$ cells/mouse) was transplanted to the subcutaneous area of back of a female BALB/c mouse of eight weeks age (body weight: about 20 g). After that, 4-hydroxy-2-cyclopentenone (0.3 mg/kg/day or 1 mg/kg/day) or 4-cyclopentene-1,3-dione (0.03 mg/kg/day or 0.1 mg/kg/day) was subcutaneously injected to the same area for a consecutive five days. On the other hand, a control group was injected with a physiological saline solution subcutaneously in the same manner. After seven days from transplantation of the cancer cells, long and short diameters of the cancer tissues formed on the back of the mouse were measured and the tumor size (mm$^3$) was calculated from a formula of (long diameter)×(short diameter)$^2$/2. Incidentally, in this test, one group consisted of eight mice.

The result is shown in Table 2. As shown in Table 2, 4-hydroxy-2-cyclopentenone and 4-cyclopentene-1,3-dione showed an anticancer activity.

TABLE 2

| Group | Dose (mg/kg/day) | Tumor Size(mm$^3$) (Mean ± SE) | Inhibiting Rate (%) |
|---|---|---|---|
| Control group | | 306 ± 37 | — |
| Group administered with 4-hydroxy-2-cyclopentenone | 1 | 161 ± 67 | 47 |
| | 0.3 | 165 ± 61 | 46 |
| Group administered with 4-cyclopentene-1,3-dione | 0.1 | 151 ± 69 | 51 |
| | 0.03 | 150 ± 62 | 51 |

Example 4

Injection Preparation.

(1) To a physiological saline solution (as regulated by the Japanese Pharmacopoeia) was added 4-cyclopentenone-1,3-dione in a concentration of 0.1% to prepare an injection preparation.

(2) To a physiological saline solution (same as above) were added 4-hydroxy-2-cyclopentenone and glycyrrhizic acid in the concentrations of 0.2% and 0.5% respectively to prepare an injection preparation.

Example 5

(1) A tablet containing 1 mg of 4-hydroxy-2-cyclopentenone and an appropriate amount of microcrystalline cellulose was prepared and coated with sugar to prepare a tablet preparation.

(2) A tablet containing 0.1 mg of 4-cyclopentenone-1,3-dione, 10 mg of dipotassium glycyrrhizate and an appropriate amount of microcrystalline cellulose was prepared and coated with sugar to prepare a tablet preparation.

Merit of the Invention

The present invention offers a pharmaceutical agent having an anticancer action and an apoptosis-inducing action selected from 4-cyclopentene-1,3-dione and 4-hydroxy-2-cyclopentenone. In addition, food or beverage where those compounds are contained therein, added thereto and/or diluted therewith is useful as food or beverage having an anticancer property and an apoptosis-inducing property.

It is also possible to study the clarification of induction of apoptosis and to develop an apoptosis inhibiting agent by the use of an apoptosis inducing agent containing the said compounds. The pharmaceutical agent of the present invention can be used for a method of inducing the apoptosis and is useful in such a use as well.

Further, according to the present invention, an inhibitor which specifically inhibits topoisomerase II where a compound having an α, β-unsaturated carbonyl group is contained as an effective component is offered. The said inhibitorisusefulasananticanceragentaswell. Furthermore, a method for inhibition of topoisomerase using a compound having an α, β-unsaturated carbonyl group offered by the present invention is useful for biochemical studies and for a screening of anticancer agents, etc.

What is claimed is:

1. A method for treating a cancer, comprising adm inistering 4-cyclopenten-1,3-dione represented by the following formula [I] and/or 4-hydroxy-2-cyclopentenone represented by the following formula [II]:

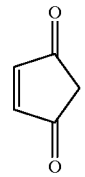

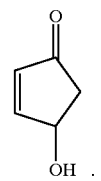

2. A method for inhibiting the growth of cancer cells, comprising administering 4-cyclopenten-1,3-dione represented by the following formula [I] and/or 4-hydroxy-2-cyclopentenone represented by the following formula [II]:

11

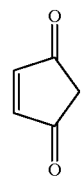

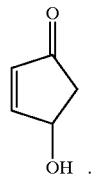

12

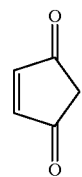

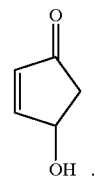

3. A method for inducing apoptosis, comprising administering 4-cyclopenten-1,3-dione represented by the following formula [I] and/or 4-hydroxy-2-cyclopentenone represented by the following formula [II]:

4. The method for inducing apoptosis according to claim 3, wherein the 4-cyclopenten-1,3-dione and/or the 4-hydroxy-2-cyclopentenone eliminate cells selected from the group consisting of virus-infected cells, cancer cells and autoreactive lymphocytes.

* * * * *

UNITED STATES PATENT AND TRADEMARK OFFICE
CERTIFICATE OF CORRECTION

PATENT NO. : 6,326,405 B1
DATED : December 4, 2001
INVENTOR(S) : Eiji Kobayashi, Nobuto Koyama and Ikunoshin Kato Page 1 of 1

It is certified that error appears in the above-identified patent and that said Letters Patent is hereby corrected as shown below:

Column 6,
Line 19, please replace "$1 \times 105^5$ cells/ml" with -- $1 \times 10^5$ cells/ml --.

Column 10,
Lines 42-43, replace "adm inistering" with -- administering --.
Line 50, to the right of the top formula graphic, insert -- [I] --.
Line 59, to the right of the bottom formula graphic, insert -- [II] --.

Column 11,
Line 5, to the right of the top formula graphic, insert -- [I] --.
Line 14, to the right of the bottom formula graphic, insert -- [II] --.

Column 12,
Line 5, to the right of the top formula graphic, insert -- [I] --.
Line 14, to the right of the bottom formula graphic, insert -- [II] --.

Signed and Sealed this

Twenty-third Day of April, 2002

*Attest:*

JAMES E. ROGAN
*Attesting Officer*  *Director of the United States Patent and Trademark Office*